US006432382B1

(12) United States Patent
Mehta

(10) Patent No.: US 6,432,382 B1
(45) Date of Patent: Aug. 13, 2002

(54) MEASUREMENT OF GASTRIC EMPTYING USING STABLE ISOTOPES

(75) Inventor: Devendra Indulal Mehta, Cherry Hill, NJ (US)

(73) Assignee: The Nemours Foundation, Wilmington, DE (US)

( * ) Notice: Subject to any disclaimer, the term of this patent is extended or adjusted under 35 U.S.C. 154(b) by 0 days.

(21) Appl. No.: 09/692,941

(22) Filed: Oct. 20, 2000

(51) Int. Cl.⁷ .............................................. A61K 51/00
(52) U.S. Cl. ........................ 424/9.1; 424/1.81; 424/9.3
(58) Field of Search .................. 424/1.81, 1.11, 424/1.73, 9.1, 9.3

(56) References Cited

U.S. PATENT DOCUMENTS

| 4,243,652 A | 1/1981 | Francis | 424/1 |
| 5,657,759 A | 8/1997 | Essen-Moller | 128/654 |
| 5,707,602 A | 1/1998 | Klein | 424/1.17 |
| 5,785,949 A | 7/1998 | Klein | 424/1.81 |
| 5,957,858 A | 9/1999 | Micheels et al. | 600/529 |
| 6,071,245 A | * 6/2000 | Kohno et al. | 600/532 |
| 6,284,219 B1 | * 9/2001 | Ajami | 424/1.11 |

* cited by examiner

*Primary Examiner*—Michael G. Hartley
(74) *Attorney, Agent, or Firm*—McGuireWoods LLP

(57) ABSTRACT

The invention provides a diagnostic test for gastrointestinal disorders by providing a safe, convenient, reliable method for measuring gastric emptying. In this test, a tracer amount of $^{13}C$-glutamine or $^{13}C$-glutamic acid is added to a liquid meal, or $^{13}C$-glutamic acid added to a solid meal. After digestion in the stomach, the meal is emptied into the small bowel, where the labeled $^{13}C$-tracer is immediately taken up and metabolized by the cells lining the small bowel. The released $^{13}CO_2$ is detected in the breath. The measurement of rise in the level of $^{13}CO_2$ as a function of time is correlated to the rate of gastric emptying.

6 Claims, 1 Drawing Sheet

MEASUREMENT OF GASTRIC EMPTYING USING STABLE ISOTOPES

BACKGROUND

I. Field of Invention

This invention relates to a diagnostic test for gastrointestinal disorders in humans to determine whether a meal being digested in the stomach is emptied into the small intestine at a normal rate. In pathologic states, the rate can be abnormally accelerated or diminished.

II. Background of Invention

During gastric emptying, ingested food is mixed with gastric juices. After appropriate dilution, the food is then emptied into the small bowel for further digestion and absorption. This is a complex, carefully regulated system involving hormones, receptors, nerves, and muscles of the stomach, and a consistent rate and concentration of the final content is emptied into the small bowel. Many factors, such as the fat composition or type of protein in the food, affect this carefully regulated emptying of liquids.

The emptying mechanism can be affected by many disorders and lead to either delayed emptying or rapid emptying (dumping). Delayed emptying can lead to symptoms of nausea, vomiting, abdominal pain, and poor growth. Dumping can lead to retching, abdominal pain, flatulence, diarrhea, poor weight gain, and dangerously low blood glucose levels. To establish a diagnosis and enable further medical management of a patient, the rate of gastric emptying often must be measured. There are various therapies for delayed or rapid emptying, but their efficacy is often unclear. The rates for emptying for solids and liquids differ. In infants and small children, the rate of liquid emptying is particularly important.

Current methods of measuring gastric emptying, called nuclear gastric emptying scans, use radioactive materials added to the milk or formula and require the patient to lie still for several hours for the scanning. Expensive nuclear imaging suites, available commonly only in major centers and with radiation safety-related requisites, are needed. In addition, the scans are not possible in those individuals who cannot lie still or are too sick to be transported to an imaging center. The patient is required to be supine, must remain still for at least an hour, and is not able to participate in normal activities. The impact of these unnatural requirements remains unclear. With radioactive scanning, test results vary according to the direction of the scan (from the front or back), and there is lack of standardization. These tests are unsuitable for infants and children because of potential risks of radiation and the need to be immobilized. Finally, because these tests use a radioactive tracer, normal values in adults as well as in children and pregnant women, are not available, making interpretations of mild abnormalities difficult.

Other methods, although not currently routinely used, using non-radioactive materials (e.g., octanoic acid and acetate with heavy carbon, $^{13}C$) have been shown to correlate with nuclear scanning. However, in every case studied so far, the tracer used must first be absorbed by the cells lining the small bowel, called enterocytes, be transported to the liver, and then be metabolized before the heavy carbon is detectable as carbon dioxide in the breath. This results in a delay in measuring the rate of gastric emptying using breath samples. Also, these materials are not currently available for clinical use for liquid gastric emptying, and their usefulness has been found to be limited to comparisons of samples within one individual. They also require complex calculations to account for the delay between their absorption and the appearance of carbon dioxide in breath.

Accordingly, there is a need for a new and improved test that is non-invasive, safe, and accurate and which can be performed with minimal inconvenience and discomfort to a patient.

SUMMARY OF THE INVENTION

The first objective of the present invention is to provide a new and improved test to measure gastric emptying that is non-invasive, safe, and accurate. The second objective is to provide a test to measure gastric emptying that can be performed in the office setting. The third objective of the present invention is to provide a test to measure gastric emptying that can be performed during normal activities without requiring the patient to lie still or be restrained. Lastly, the fourth objective is to provide a test to measure gastric emptying that can be repeated frequently without risk.

These objectives are attained in the present invention which provides a new method for measuring gastric emptying in which $^{13}C$-glutamine or $^{13}C$-glutamic acid is administered orally to a patient and breath samples are taken from the patient at periodic intervals and analyzed for carbon dioxide. More particularly, at least one breath sample is taken prior to the administration of the $^{13}C$-glutamine or $^{13}C$-glutamic acid and at least one sample is taken subsequent to the administration of the $^{13}C$-tracer (e.g., the $^{13}C$-glutamine or $^{13}C$-glutamic acid) and the method for analyzing for carbon dioxide can distinguish between $^{12}C$-carbon dioxide and $^{13}C$-carbon dioxide and at least measure the relative amounts of $^{12}C$-carbon dioxide and $^{13}C$-carbon dioxide.

DETAILED DESCRIPTION OF THE INVENTION

Figure 1:
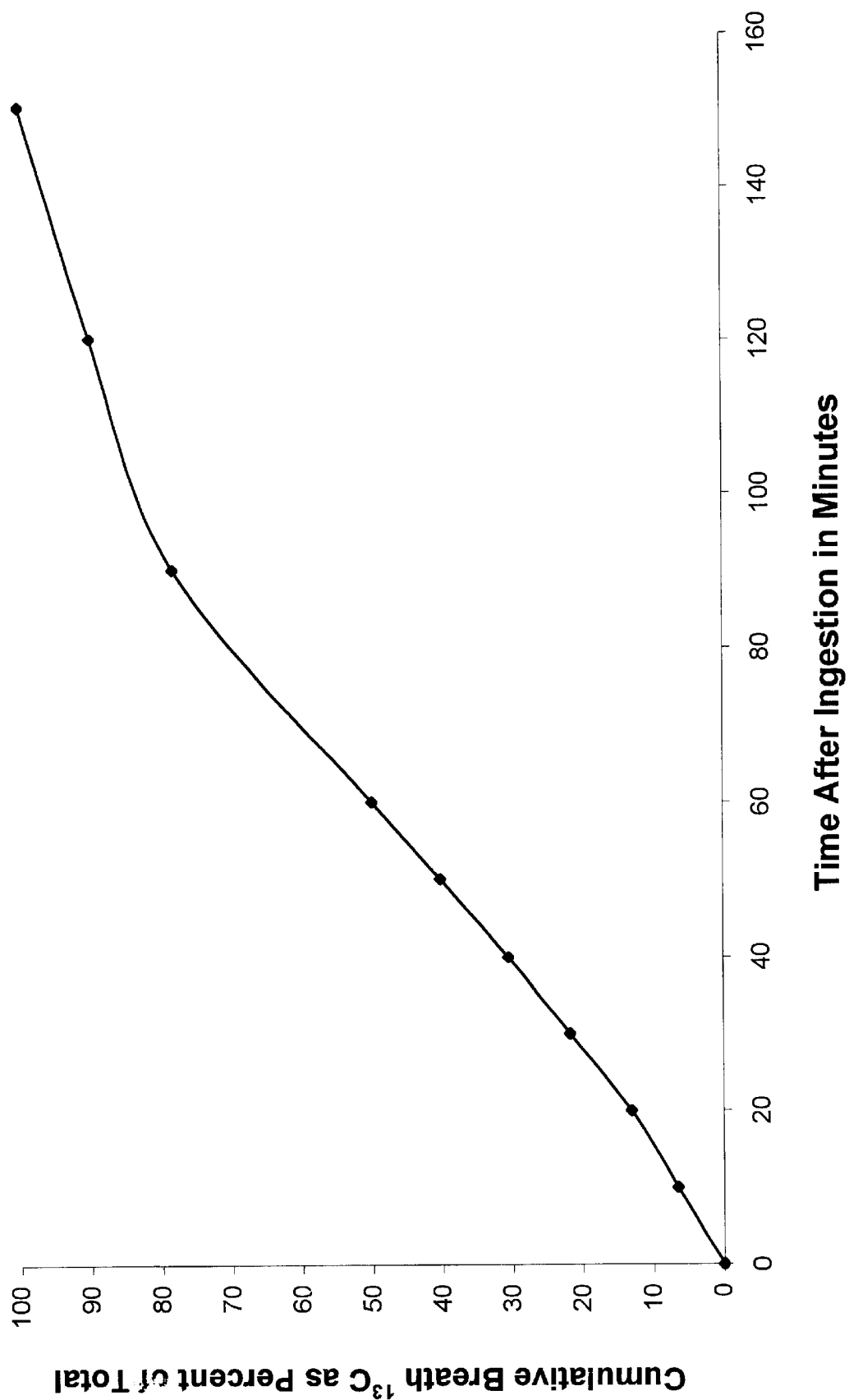
FIG. 1 shows a plot of the cumulative $^{13}C$ atoms excess over baseline in breath plotted against time after ingestion. The curve represents gastric emptying and is used to calculate the 60-minute emptying time and the half-emptying time.

The non-invasive, safe method of the measuring gastric emptying of the present invention can be performed in an office setting, does not require restraint of the patient and may be repeated frequently without risk. The method is based on the fact that both glutamine and glutamic acid are rapidly metabolized at the small bowel brush border to carbon dioxide amongst other products. Glutamine is the preferred fuel of the enterocytes, while glutamic acid has also been recently shown to undergo almost complete first pass metabolism by the enterocyte. Therefore, the liberated carbon dioxide appears in the breath quickly which results in improved efficiency in the measurement of the carbon dioxide. When $^{13}$C-glutamine or glutamic acid is used as the tracer, the increase in $^{13}$C over $^{12}$C in the breath carbon dioxide reflects the emptying from the stomach. Due to the efficiency of measuring carbon dioxide produced from the tracers, complex data handling is not required. Additionally, because glutamine and glutamic acid are metabolized throughout the small bowel, the test is more likely to be reliable even when emptying is rapid.

The use of $^{13}$C-glutamine or $^{13}$C-glutamic acid offers the further advantage that no nuclear scanning is required with its use. Thus, the risk of radiation is eliminated, and the patient is neither required to lie supine for long periods of time nor are restraints required.

As used in this discussion glutamic acid is taken to mean either the free acid or a salt of glutamic acid.

In one embodiment of the method a breath sample is obtained from a patient to serve as a baseline sample. The baseline sample is important as it allows increase from ambient $^{13}$C to be estimated. Then a tracer amount of $^{13}$C-glutamine or $^{13}$C-glutamic acid which has been added to a liquid is administered orally to the individual. Suitable liquids for use as a carrier for the $^{13}$C-tracer include but are not limited to milk, infant formula, or indeed any dietary liquid chosen to be evaluated. In embodiments for measuring solid gastric emptying, $^{13}$C-glutamic acid (or the sodium salt, sodium $^{13}$C-glutamate) in tracer amounts can be added to the food to be cooked. For example, traditionally a freshly cooked egg sandwich has been used for measuring solid gastric emptying, but as one skilled in the art will recognize the method is equally applicable for use with other solid foods. Glutamic acid, but not glutamine, is readily soluble, soliciting distribution of the tracer in the food.

Breath samples are obtained from the patient at regular intervals for a period of time after ingestion of the $^{13}$C-tracer and the time interval between taking the sample and the ingestion of $^{13}$C-tracer is recorded. Typically, samples are acquired over about a one to three hour period following ingestion at a sampling rate of one sample about every ten minutes, for example. The total number of breath samples taken, the time interval over which samples are taken and the time interval between taking each sample may be varied to accommodate patient individuality with the critical requirements being that breath samples be collected and that the time of collection relative to the ingestion of $^{13}$C-glutamine is known.

For example, breath samples may be collected in a Quintron (Milwaukee, Wis.) breath sampling bag made of aluminum, with a tubing that houses a one way valve. The device includes a second, soft plastic bag attached to the tubing that serves to collect the deadspace air when air is blown into the tube. For subjects unable to blow into the tube, a face mask may be used. In addition, for small infants who do not generate enough exhaled air, a side port may be used to aspirate air upon exhalation, and the total amount of exhaled air needed collected over 4 or 5 breaths. As one skilled in the art will recognize this is an example of an apparatus and methods for obtaining breath samples and other methods of collecting breath samples are equally applicable to the method of this invention.

The collected breath samples including the at least one baseline sample are analyzed for carbon dioxide by a method which can detect carbon dioxide, distinguish between $^{13}$C-carbon dioxide and $^{12}$C-carbon dioxide and at least determine the relative amounts of $^{13}$C-carbon dioxide and $^{12}$C-carbon dioxide. One example of a method suitable for analyzing the breath samples is isotope ratio mass spectrometry. Such a method is described in Schoeller D A, Schneider J F, Solomons N W, Watkins J B, Klein P D. Clinical Diagnosis with the Stable Isotope (13)C in CO(2) Breath Tests: Methodology and Fundamental Considerations. J Lab Clin Med 1977;90:412–21, incorporated herein in its entirety by reference.

From the data obtained the enrichment of heavy carbon ($^{13}$C) is determined as a relative difference between the sample and the international limestone standard of Pee Dee belemnite. The atoms excess of heavy carbon ($^{13}$C) from baseline for each sample is plotted as a function of the time interval between ingestion of $^{13}$C-tracer and taking the breath sample. The curve obtained may be extrapolated to baseline as necessary. The $^{13}$C-tracer emptied into the small bowel over time results in excess $^{13}$C. The total $^{13}$C (and also the cumulative $^{13}$C) is estimated from the area under the curve, and is proportional to the amount of tracer emptied, and hence gastric emptying. Thus, the cumulative amount in the breath at 60 minutes as a percent of the total gives the 60-minute emptying time. Additional parameters, including the half-emptying time, can also be derived from this curve. This can be determined from a linear semilogarythmic plot of emptying against time, and the time taken to halve the gastric contents from 100 percent to 50 percent estimated from the plot. Alternatively, curve fit models typically used for radionucleotide scanning can also be applied to the $^{13}$C cumulative curve that represents gastric emptying.

FIG. 1 shows an example of the a plot of cumulative Breath $^{13}$C as a percent of total Breath $^{13}$C verses time after ingestion. The curve demonstrates typical sigmoid characteristics of a liquid emptying curve. To enable 60 minute emptying to be calculated, the test needs to be continued until most of the Breath $^{13}$C is collected, in most cases about 2 to 3 hours, so that total can be estimated.

The unique role of glutamine and glutamic acid as fuels for the cells lining the small bowel improves the correlation between time of appearance of the heavy carbon in breath and the emptying of glutamine from the stomach into the small bowel. Furthermore, in keeping with amino acids in general, any amount of labeled tracer that may not be metabolized immediately by the enterocyte, will be stored in the post meal state, so that subsequent liberation of $^{13}$C in the post prandial time will be minimized. This enhances the test's utility by allowing direct assessment of the gastric emptying characteristics, minimizing the test's duration compared to other stable isotopes, such as octanoic acid which require up to 6 hours collections, and resulting minimal secondary $^{13}$C production.

Further, the test is noninvasive and does not require the restraints, special equipment, and radioisotopes needed with current methods of testing. Thus, the test is useful for all patients including infants and children and pregnant women.

EXAMPLE

The following example is presented as one example of the practice of the method of the invention and as such is illustrative of only one of many possible ways to practice the invention.

For measuring gastric emptying thirty milligrams of $^{13}$C-glutamine powder was added to a suitable liquid carrier such as infant formula or milk with the amount of liquid being one ounce per kilogram of body weight to a maximum of 8 oz. The $^{13}$C-glutamine and liquid were mixed thoroughly with shaking and then administered to the patient over 10 minutes on an empty stomach. Breath samples were collected before ingestion and at 10, 20, 30, 40, 50, 60, 90, 120, 150, and 180 minutes after ingestion of the $^{13}$C-glutamine mixture using a breath sampling kit (Quintron, Milwaukee, Wis.). The samples were analyzed by isotope ratio mass spectroscopy for the excess heavy carbon to normal carbon ratio ($^{13}$C: $^{12}$C ratio). The atoms excess $^{13}$C were recorded for each time point, and the curve was extrapolated to baseline as necessary. An estimation of the area under the curve yielded cumulative atoms excess, which represents the gastric emptying curve. The cumulative amount in the breath at 60 minutes as a percent of the total gives the 60-minute emptying time (see FIG. 1). Additional parameters, including the half-emptying time, can also be derived from this curve.

It will be readily understood by those persons skilled in the art that the present invention is susceptible to broad utility and application. Many embodiments and adaptations of the present invention other than those herein described, as well as many variations, modifications and equivalent arrangements, will be apparent from or reasonably suggested by the present invention and foregoing description thereof, without departing from the substance or scope of the invention.

Accordingly, while the present invention has been described here in detail in relation to its preferred embodiment, it is to be understood that this disclosure is only illustrative and exemplary of the present invention and is made merely for the purposes of providing full and enabling disclosure of the invention. The foregoing disclosure is not intended to be construed or to limit the present invention or otherwise to exclude any other such embodiments, adaptations, variations, modifications and equivalent arrangements, the present invention being limited by the claims and the equivalents thereof.

What is claimed is:

1. A method of measuring gastric emptying comprising:

collecting at least one baseline breath sample from a patient;

administering a $^{13}$C-glutamine composition orally to the patient;

collecting at least one test breath sample from the patient at a known interval after administering the $^{13}$C-glutamine composition;

analyzing the at least one baseline breath sample and the at least one test breath sample for the relative amount of $^{13}$C present in the at least one baseline breath sample and the at least one test breath sample; and correlating the relative amount $^{13}$C as a function of time to the rate of gastric emptying for the patient.

2. A method of measuring gastric emptying comprising:

collecting at least one baseline breath sample from a patient;

administering a $^{13}$C-glutamic acid composition orally to the patient;

collecting at least one test breath sample from the patient at a known interval after administering the $^{13}$C-glutamic acid composition;

analyzing the at least one baseline breath sample and the at least one test breath sample for the relative amount of $^{13}$C present in the at least one baseline breath sample and the at least one test breath sample; and correlating the relative amount of $^{13}$C as a function of time to the rate of gastric emptying for the patient.

3. The method of claim 2, wherein the $^{13}$C-glutamic acid is dissolved in a liquid.

4. The method of claim 2, wherein the $^{13}$C-glutamic acid is added to the composition of a solid meal.

5. A method of measuring gastric emptying comprising:

administering a $^{13}$C-glutamine composition to the patient;

analyzing at least one test breath sample for an amount of $^{13}$C present in the at least one test breath sample as a function of time; and correlating the amount $^{13}$C as a function of time to the rate of gastric emptying for the patient.

6. A method of measuring gastric emptying comprising:

administering a $^{13}$C-glutamic acid composition to the patient;

analyzing at least one test breath sample for an amount of $^{13}$C present in the at least one test breath sample as a function of time; and correlating the amount $^{13}$C as a function of time to the rate of gastric emptying for the patient.

* * * * *